US010357169B2

(12) United States Patent
Hu et al.

(10) Patent No.: US 10,357,169 B2
(45) Date of Patent: Jul. 23, 2019

(54) METHODS FOR DETERMINING WHETHER PATIENT MONITOR ALARMS ARE TRUE OR FALSE BASED ON A MULTI RESOLUTION WAVELET TRANSFORM AND INTER-LEADS VARIABILITY

(71) Applicant: THE REGENTS OF THE UNIVERSITY OF CALIFORNIA, Oakland, CA (US)

(72) Inventors: Xiao Hu, San Francisco, CA (US); Rebeca Salas-Boni, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 146 days.

(21) Appl. No.: 15/332,821

(22) Filed: Oct. 24, 2016

(65) Prior Publication Data
US 2017/0100048 A1    Apr. 13, 2017

Related U.S. Application Data

(63) Continuation of application No. PCT/US2015/027663, filed on Apr. 24, 2015.
(Continued)

(51) Int. Cl.
A61B 5/04        (2006.01)
A61B 5/0464    (2006.01)
A61B 5/00        (2006.01)

(52) U.S. Cl.
CPC ...... A61B 5/04012 (2013.01); A61B 5/04015 (2013.01); A61B 5/0464 (2013.01);
(Continued)

(58) Field of Classification Search
CPC . A61B 5/04012; A61B 5/0464; A61B 5/7221; A61B 5/726; A61B 5/7242
See application file for complete search history.

(56) References Cited

U.S. PATENT DOCUMENTS 8,295,567 B2    10/2012    Watson et al.
2008/0109041 A1*  5/2008   de Voir .............. A61B 5/04017
                                                    607/7
(Continued)

FOREIGN PATENT DOCUMENTS

JP      5324743 B2       10/2013
WO    2009-039278 A1    3/2009

OTHER PUBLICATIONS

Korean Intellectual Property Office (KIPO), International Search Report and Written Opinion, dated Jul. 31, 2015, related PCT International Application No. PCT/US2015/027663, pp. 1-12, with claims searched, pp. 13-17. The relevance of non-English language reference JP 5324743 is indicated therein and a separate concise explanation is not required.

Primary Examiner — Alyssa M Alter
(74) Attorney, Agent, or Firm — O'Banion & Ritchey LLP; John P. O'Banion

(57) ABSTRACT

Methods for automatically determining whether a patient monitor alarm will sound from a true or false signal, in particular from ventricular tachycardia (VT) and suppressing false alarms without eliminating any true alarms are presented. A multiresolution wavelet is extracted from a raw ECG waveform. Features are then extracted from the wavelets that account for summary statistics, noise, areas under the curve and summary statistics of the KL-divergence of the power spectra density between every two ECG leads. A classifier can be then be trained and its performance measured.

20 Claims, 12 Drawing Sheets

Related U.S. Application Data

(60) Provisional application No. 61/984,167, filed on Apr. 25, 2014.

(52) U.S. Cl.
CPC ............ *A61B 5/7221* (2013.01); *A61B 5/726* (2013.01); *A61B 5/7242* (2013.01)

(56) References Cited

U.S. PATENT DOCUMENTS

2012/0179055 A1 7/2012 Tamil et al.
2012/0197831 A1 8/2012 Dong et al.

* cited by examiner

METHODS FOR DETERMINING WHETHER PATIENT MONITOR ALARMS ARE TRUE OR FALSE BASED ON A MULTI RESOLUTION WAVELET TRANSFORM AND INTER-LEADS VARIABILITY

CROSS-REFERENCE TO RELATED APPLICATIONS

This application is a 35 U.S.C. § 111(a) continuation of PCT international application number PCT/US2015/027663 filed on Apr. 24, 2015, incorporated herein by reference in its entirety, which claims priority to, and the benefit of, U.S. provisional patent application Ser. No. 61/984,167 filed on Apr. 25, 2014, incorporated herein by reference in its entirety. Priority is claimed to each of the foregoing applications.

The above-referenced PCT international application was published as PCT International Publication No. WO 2015/164833 on Oct. 29, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to a method for reducing false alarms by patient monitors, and more particularly to a method for determining whether a ventricular tachycardia (VT) monitor alarm is true or false before the alarm sounds based on a multiresolution wavelet transform and inter-leads variability.

2. Background Discussion

Over the past few years, reducing the number of false positive patient monitor alarms (FAs) in the Intensive Care Unit (ICU) has become an issue of the utmost importance. ICU cardiac FA rates of up to 83% have been reported, leading to both an increase in the workload of healthcare providers and their desensitization to alarms. In addition to patient monitor alarm fatigue in healthcare providers, patients are often disturbed by the noise of the alarms sounding. Furthermore, a high incidence of FAs can cause disruptions in patient care.

Methods for automatically detecting cardiac FAs using algorithms have been developed recently and have had successful suppression rates for most cardiac arrhythmias. However, the most challenging false arrhythmia alarms to suppress are for ventricular tachycardia (VT) because the false alarm reduction rate for VT alarms is the least among other types of arrhythmias.

Different approaches have been employed to reduce the burden of cardiac FAs. One approach is to determine the quality of the ECG signal, based on the premise that noisy signals tend to trigger false alarms. There are several ways of measuring signal quality including, statistical measures, agreement between different algorithms for beat detection, and spectral decomposition of the local signal segment.

Another approach consists of incorporating extra non-ECG waveform data, such as invasive arterial blood pressure (ABP) and photoplethysmogram (PPG) obtained from pulse oximetry. The driving principle of this approach is to corroborate the ECG signal using another signal that is correlated to the ECG signal and is provided by an independent sensor. The features of novel signal quality indices (SQIs) are extracted using dynamic time wrapping (DTW) to create a template of the signals, as well as an estimation of the heart rate (HR) using ECG, PPG and ABP. A generic algorithm is then used to reduce the number of features and a trained Relevance vector machine is used as a classifier.

Several of these and similar approaches require additional signals including, ABP, PPG and central venous pressure (CVP) or pulmonary arterial pressure (PAP). Many utilize a nonlinear joint dynamical model and use Baysian filters as classifiers. However, these approaches are computationally intensive and require powerful computers to run in near real time.

BRIEF SUMMARY

Embodiments of the present disclosure can avoid the shortcomings of traditional patient monitor false alarm (FA) detection by providing a method for suppressing FAs, specifically false ventricular tachycardia (VT) monitor alarms, without suppressing true VT monitor alarms, using only ECG waveforms. This can be useful in settings outside of the ICU where other waveforms obtained by invasive means are not readily available.

Embodiments consistent with the present disclosure may apply a multiresolution wavelet transform to ECG waveform data to reduce dimensionality of the data and separate it into different and more useful frequencies. Measurements can be extracted from this lower dimensional representation of the raw ECG signal, known as its wavelet transform. Features can be extracted from the wavelet transform, including the variability within measurements among the different patient monitor leads to determine whether an alarm is true or false.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

Figure 1:
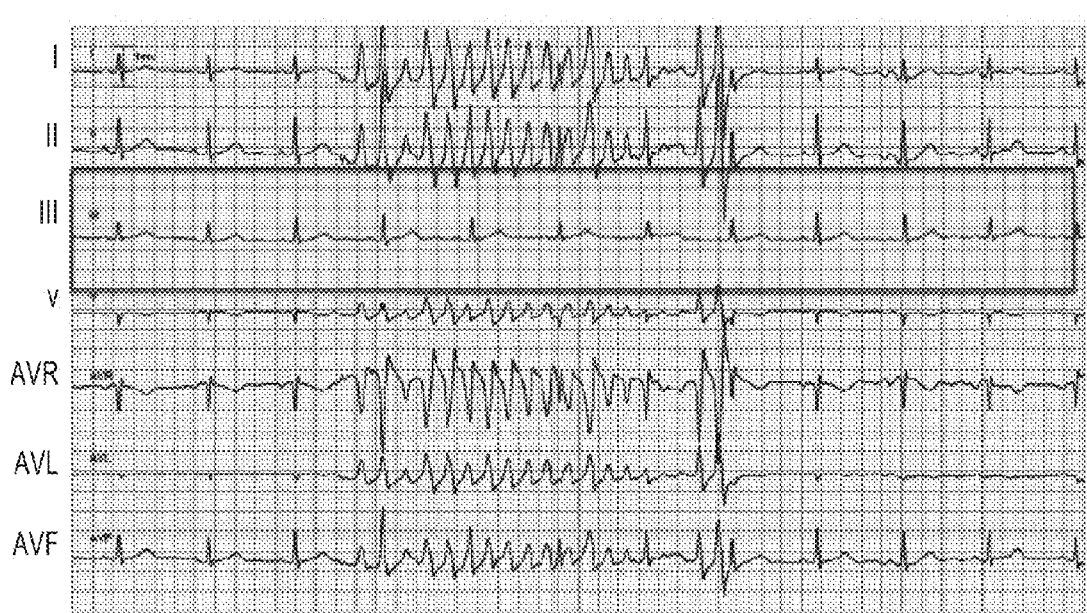
FIG. 1 is an ECG printout of ECGs from 7 ECG leads, with the one normal sinus rhythm outlined.

Described herein are methods for evaluating whether ECG signals will cause cardiac monitors to produce false alarms so that the alarm can be suppressed before it sounds, thus preventing alarm fatigue in health care providers. The present method can be used to distinguish true and false ventricular tachycardia (VT) monitor alarms, which is challenging because VT arrhythmias produce highly irregular ECG waveforms that can mimic an artifactual ECG signal. Although embodiments of the method described herein were designed with the need for detecting false VT alarms in mind, this method can be used to reduce the number of false monitor alarms caused by various other arrhythmias and patient monitor signals.

By way of example and not limitation, embodiments of the method can be carried out by applying a multiresolution wavelet transform to the ECG waveform data. This process reduces the dimensionality of the data and separates it into different frequencies, allowing isolation of the most useful frequencies for diagnosis, as well as denoising of the signal.

From this lower dimensional signal (wavelet transform), specific features can be extracted. For example, features corresponding to statistics from the wavelet decomposition which correspond to different frequencies and how these vary between ECG leads can be extracted. Features that account for the noise in the signal can be extracted, with the idea that the noisier signals produce false alarms. Also, statistics from the largest areas measured within small time intervals can be used for input in order to capture the ventricular beats. As described in the example, a classifier can be trained and its performance measured.

Thus, the algorithm can be designed by combining the two approaches of (1) extracting measurements not from the signal itself, but from a lower dimensional representation or wavelet transform, and (2) using the variability within measurements in different patient monitor leads to decide whether an alarm is true or false. This allows for an algorithm that can be applied to the variable number and types of leads available for a patient at the time of the monitor alarm.

Referring more specifically to the drawings, for illustrative purposes, embodiments of the method for determining whether a patient monitor alarm is true or false based on a multi resolution wavelet transform and inter-leads variability are described herein and depicted generally in FIG. 1 through FIG. 12. It should be appreciated that the methods may vary as to the specific steps and sequence without departing from the basic concepts as disclosed herein. The method steps are merely exemplary of the order that these steps may occur. The steps may occur in any order that is desired, such that it still performs the goals of the claimed technology.

In recent years, wavelet transforms have been applied to solve several problems with ECG signals, such as heart beat classification and automatic segmentation, obtaining very promising results. The method of the embodiment described in the following example is based on features extracted from a decomposed ECG signal at approximately 20 seconds prior to a triggered heart monitor alarm. No other physiological waveforms were used. A multi resolution wavelet transform was applied to the ECG data and features from approximately chosen scales were extracted and combined across all available leads. Features extracted from this decomposition were presented to a L1-regularized Logistic Regression classifier to label VT monitor alarms as true or false.

The algorithm can be integrated into existing patient monitors as an added step following the current alarm algorithm to prevent the sounding of an alarm that is classified as false by the presently disclosed method. The algorithm can also be used as an alarm filter in other applications that require alarms from patient monitors as input for further data processing or visualization. In this way, it would not prevent monitors from sounding alarms, even when they are classified as false.

The results of testing the algorithm on two datasets of physiological waveforms are presented in the example below. To find VT signal data, the cardiac monitor alarms were manually assessed and annotated as true or false by a group of expert clinicians and nurse scientists at UCSF, using only ECG signals.

Example

Two datasets were used to test the efficacy of VT monitor FA suppression using embodiments of the presently described method: (1) a dataset from the UCSF—General Electric (GE) Alarm Study, and (2) a subset of the Multi-parameter Intelligent Monitoring in Intensive Care (MIMIC) II dataset. For the UCSF-GE dataset, all available physiological monitoring data was automatically stored for all consecutive patients treated in the 5 adult intensive care units during the 31 day period of March, 2013. All patients signed patient consent documents, approved by the UCSF institutional review board. The database contained multi-parameter physiologic waveforms collected from 461 patients which were all sampled at 240 Hz. The waveforms were compiled using the BedMasterEx system (Excel Medical Electronics, Jupiter, Fla.), which archived continuous waveform data from 77 General Electric bedside monitors (GE Healthcare, Waukesha, Wis.). The creation of this database is part of the ongoing Alarm Study by UCSF and GE. Each record contains a varying number of channels of continuously monitored waveforms, as well as monitor-generated alarms. The ECG signals available were: leads I, II, III, V (usually V1), aVL, aVR and aVF.

Alarms for 6 arrhythmias were manually annotated as "True" or "False" by a group of expert clinicians and nurse scientists at UCSF. A total of 12,674 alarms were annotated, including ASYSTOLE, VFIB/VT, VT, V-BRADY, ACC VENT and PAUSE. Overall, 87% of the alarms were false. In the case of VT, a total of 3,860 alarms were annotated, out of which 533 were labeled as true, giving a true alarm rate of 13.8%. There were 3,314 false VT alarms (85.9% of all the annotated VT alarms) and 13 VT alarms (0.3%) were deemed unanalyzable.

Three patients accounted for 2,732 (70.8%) of all the VT alarms. The patient who generated 45.3% of the total alarms had 1,269 VT alarms, one of which was true. The patient who generated 9.6% of the total alarms had 1,129 VT alarms, of which only the last three, immediately prior to death, were true. The third patient had 334 VT alarms, all true, due to a ventricular episode, often called an "electrical storm," which is a life-threatening condition defined by 3 or more episodes of sustained VT within 24 hours. Removing the alarms corresponding to these three patients left 1,128 alarms, of which 195 were true, yielding a 17.3% true alarm rate. A subset of alarms from these three patients was sampled so that the dataset contained 1,273 alarms, of which 10% were true, as shown in Table 1. Most of the patients had all seven uninterrupted ECG signals available during the 20 seconds prior to the alarm. The patients' data was divided into a training set and a test set. Approximately 10% of the VT alarms corresponding to each set were true.

The second dataset was collected from PhysioNet's MIMIC II Version 2, a multi-parameter ICU database, sampled at 125 Hz, where physiologic signals and vital signs time series were also captured from patient monitors. Data was collected from between 2001 and 2007 from a variety of ICUs (medical, surgical, coronary care and neonatal). Records with up to eight signals, which corresponded to record names beginning with a44 trough a46, were located. This subset of data was selected because it had the largest number of ECG signals available at the time of the alarm. The more ECG leads available to collect signals, the better the diagnosis. This is because certain characteristics in ECG waveforms, which are of diagnostic value, can only be detected by certain leads for a given subject. FIG. 1 shows an ECG printout of ECGs from 7 ECG leads, with the one normal sinus rhythm outlined.

Figure 2A:
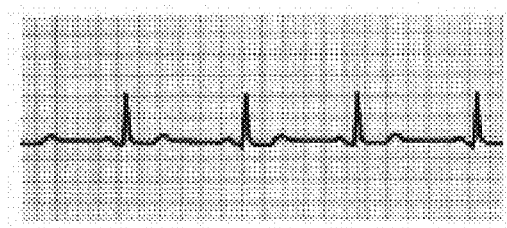
FIG. 2A is an ECG printout of a normal sinus rhythm.
Figure 2B:
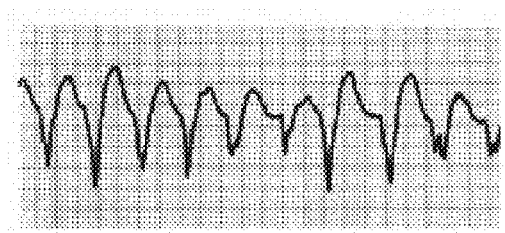
FIG. 2B is an ECG printout of ventricular tachycardia (VT).
Figure 3A:
FIG. 3A through FIG. 3D are ECG printouts of ECG signals that produced false VT alarms.
Figure 3B:
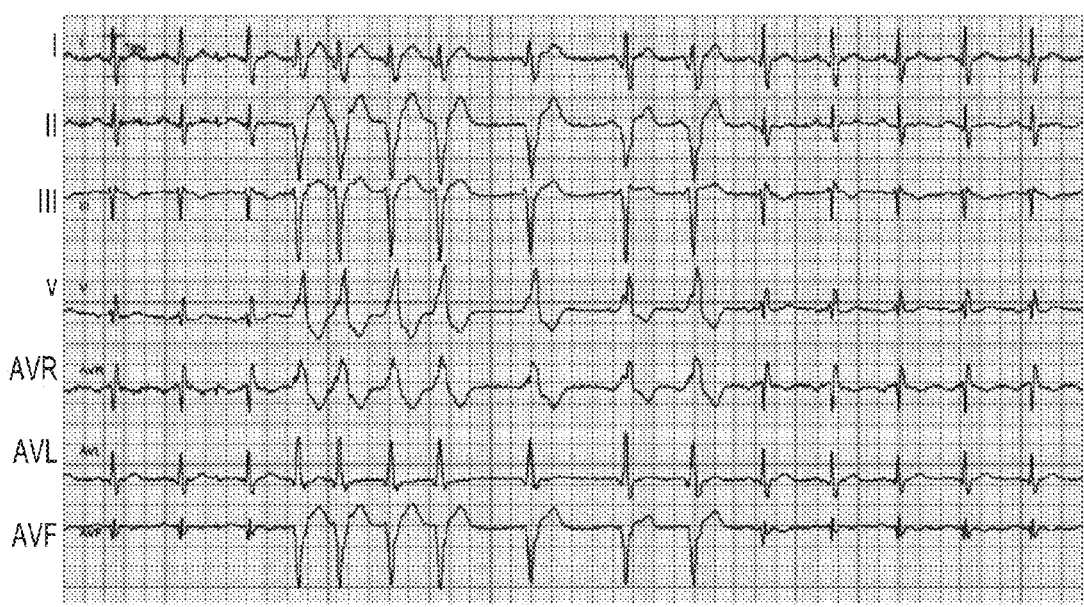
Figure 3C:
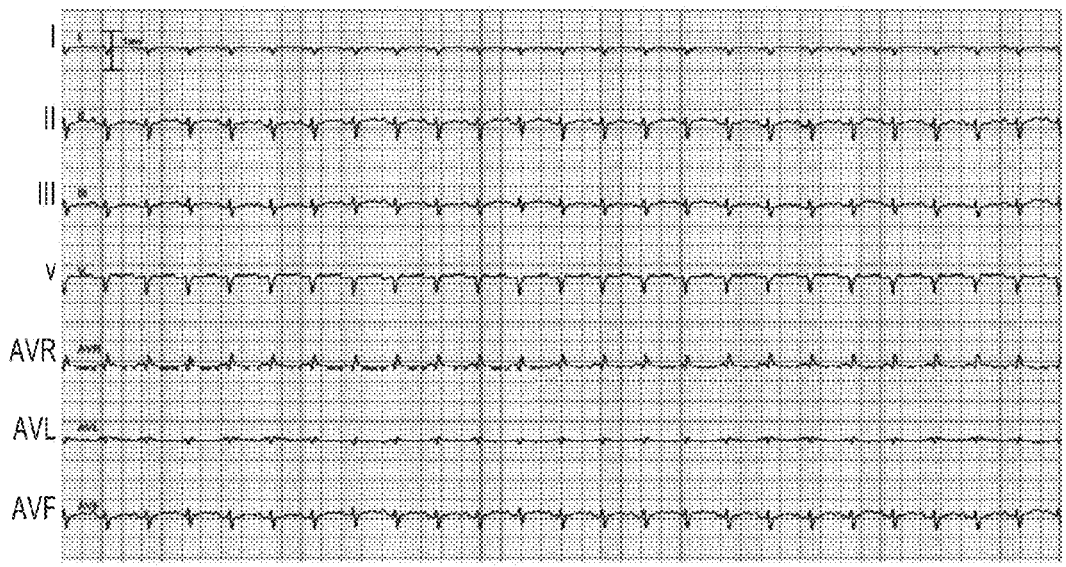
Figure 3D:

FIG. 2A depicts an ECG of a normal sinus rhythm. FIG. 2B shows an ECG of VT. VT can be defined as a rapid heartbeat with at least 6 beats at a rate of more than 100 beats per minute.

Most of the patients' data in this subset had three uninterrupted ECG signals available during the 20 seconds prior to the alarm. There were 88 records and a total of 1,088 VT alarms, of which 298 (27%) were true positives. Of these 1,088 VT alarms, only the alarms that had three ECG leads being recorded without interruption or missing data for the 20 seconds prior to the alarm were used. This reduced the number of VT alarms to 1,022. The patients' data was further divided into two disjointed sets. The VT alarms corresponding to each dataset contained approximately 27% true alarms, as were in the total dataset.

For the algorithm, an approximately 20 second signal prior to the alarm is extracted. The baseline wander and noise are removed from the signal and a wavelet transform is applied to separate each ECG signal into different frequency bands. Different features from different frequencies are then extracted.

Only ECG signals were considered for the algorithm in this example. The MIMIC II data was upsampled to 250 Hz. For both the upsampled MIMIC II database and the UCSF-GE database, each ECG block was sequentially filtered by a high-pass filter with a cutoff frequency at 0.5 Hz, a notch filter for removing power-line noise and a band-pass filter between 1 and 35 Hz. A 20 second analysis window prior to the alarm onset was considered for the algorithm. In order to comply with the regulations of the AAMI (Association for the Advancement of Medical Instrumentation), a patient alarm must be triggered, at most, 10 seconds after an event. Therefore, using a signal that lasts for 20 seconds most likely captures the event that triggered the alarm.

Given the characteristics of both true and false VT alarms observed in the UCSF-GE Alarm Study, it was concluded that the extracted features should:

(1) Be able to detect if a signal satisfies the definition of VT. That is, a run of 6 or more ventricular beats at a rate of greater than 100 beats per minute;

(2) Capture the amount of noise in the signal; and (3) Determine whether there is variability among ECG leads. It was often observed that one ECG lead would show a clear sinus rhythm while the remaining ECG leads showed artifacts mimicking VT, which led the existing GE (General Electric) algorithm to detect a VT event. FIG. 3A through FIG. 3D show ECG printouts of ECG signals that produced false VT alarms. Each row (I, II, III, V, AVR, AVL, AVF) represents a reading from a different ECG lead. The variability among leads can be seen in these examples.

The feature extraction process for the algorithm consists of two steps. First, the measurements are extracted not from the signal itself, but from its wavelet transform, which makes it possible to isolate specific frequency bands of the ECG signal. Second, the variability within measurements in different leads can be used to decide whether an alarm will be true or false. This allows for an algorithm that can be applied to the variable number and types of leads available for a patient at the time of the alarm. The feature extraction was performed using MATLAB R2013a.

Figure 4:
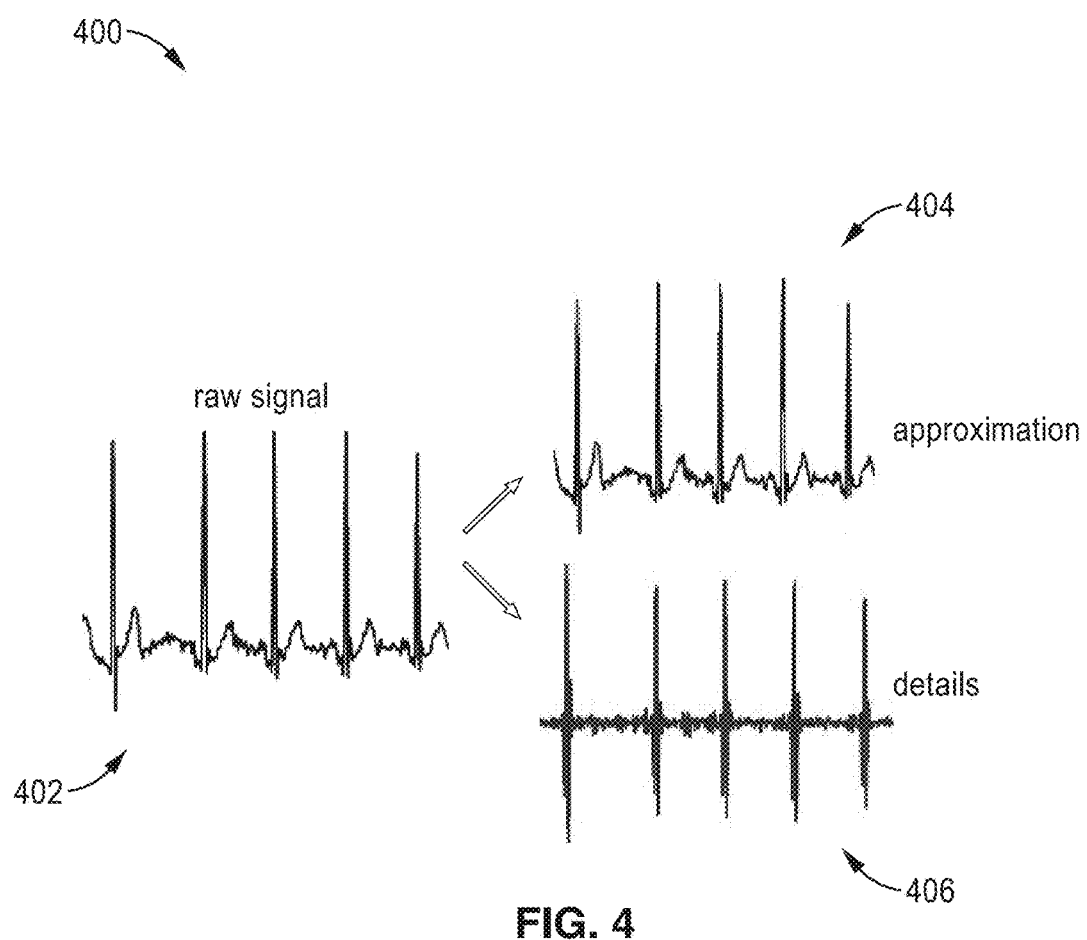
FIG. 4 is a schematic diagram of a raw signal being split into an approximation wavelet and a details wavelet using a Discrete Wavelet Transform (DWT).

Wavelet transforms decompose a signal into a set of "frequency bands," or scales, by projecting the signal into wavelets (a set of basic functions). Referring to FIG. 4, in this example, a Discrete Wavelet Transform (DWT) 400 was used. A DWT 400 splits a raw or original signal 402 into two signals: its approximation wavelet (WA1) 404 and its details wavelet (WD1) 406. WA1 404 and WD1 406 are half the length of the original signal 402. WA1 404, the approximation, is the coarser representation of the signal and WD1 406, the details, are the noisy components of the original signal 402.

Figure 5A:
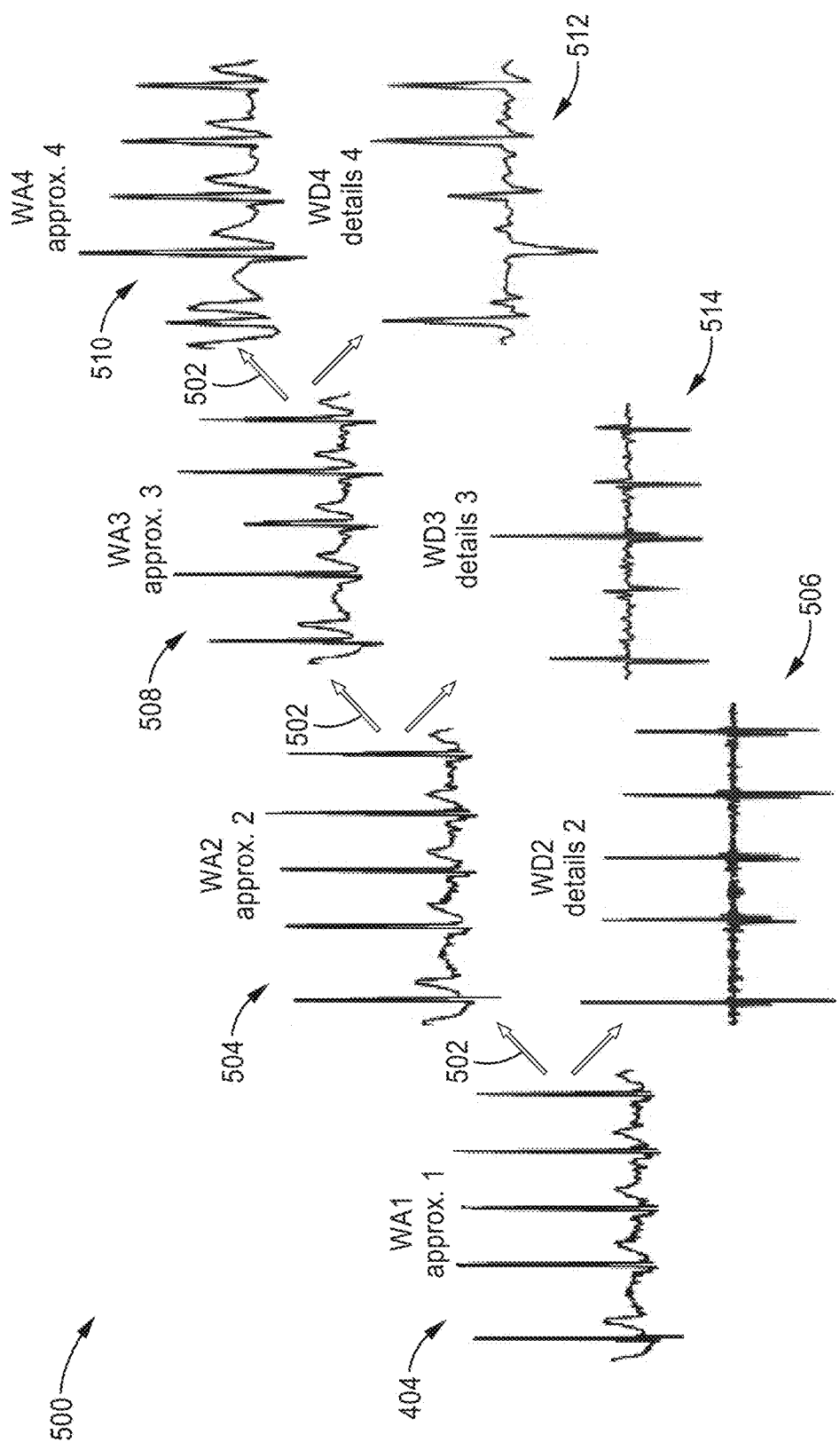
FIG. 5A is a schematic diagram of a wavelet transform multiresolution process.
Figure 5B:
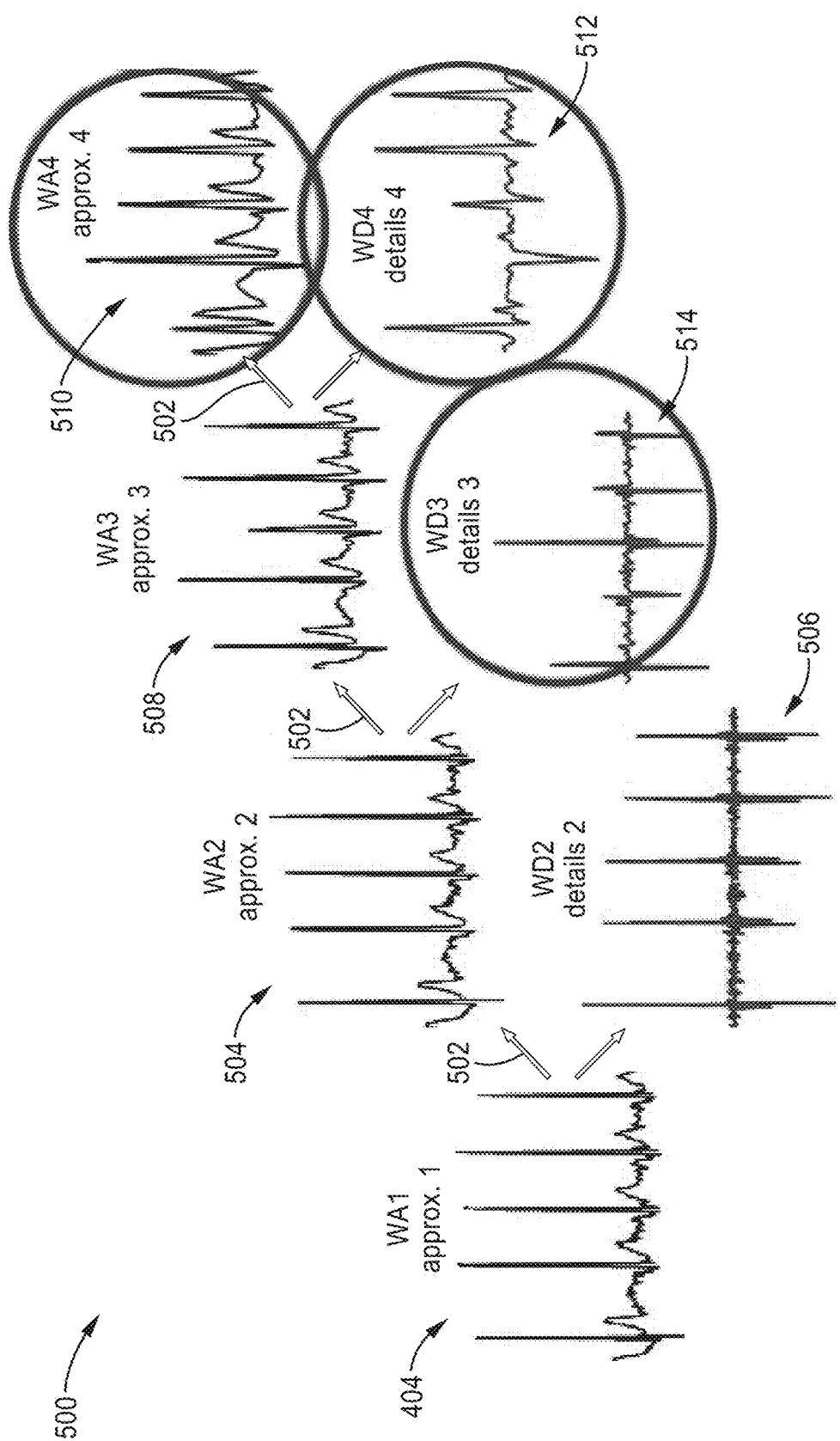
FIG. 5B is a schematic diagram of the wavelets that were used in an embodiment of the present disclosure.

Referring to FIG. 5A, the multiresolution process 500 includes repeatedly decomposing 502 the wavelet approximation signal (WA1) 404 into two signals: a new approximation wavelet signal (WA2) 504 and a new detail wavelet signal (WD2) 506. In this example, a 4-level multiresolution wavelet transform was applied using the wavelet Daubechies 2, wherein the new approximation signals 504, 508 are further decomposed. FIG. 5B shows the signals that were used for the algorithm described in the present example: the fourth approximation wavelet (WA4) 510, the fourth details wavelet (WD4) 512 and the third details wavelet (WD3) 514.

Figure 6:
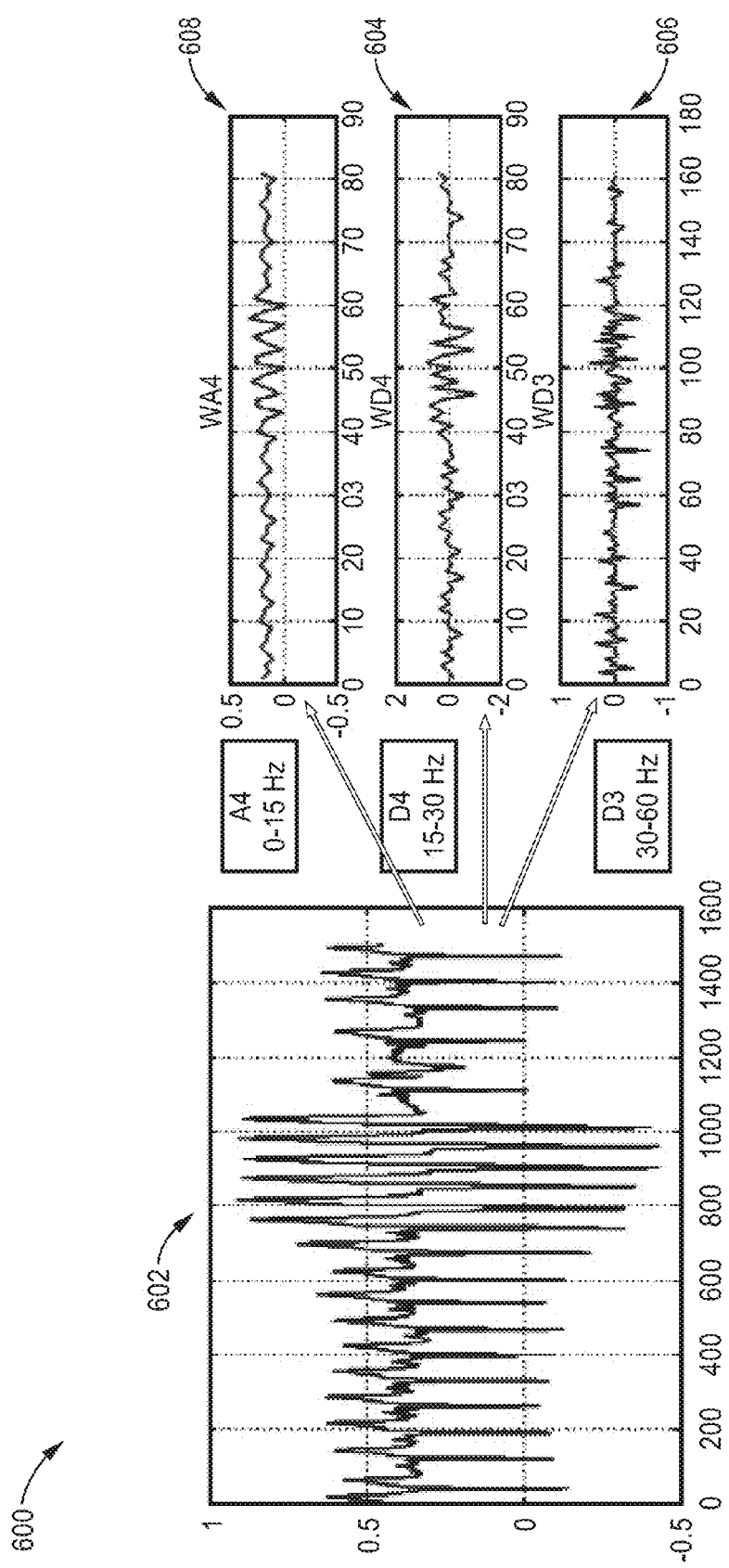
FIG. 6 is an image of the decomposition of six seconds of a raw ECG signal corresponding to a true VT alarm.

Most of the energy of the ECG signal lies between 0.5 Hz and 40 Hz. The frequency spectrum of individual QRS complexes is found in the range of 0-20 Hz and it has maximum amplitude at 4 Hz in VT. FIG. 6 shows the decomposition 600 of six seconds of a raw ECG signal 602 corresponding to a true VT alarm. The coefficients corresponding to signals WD4 604, WD3 606 and WA4 608 were retained, which correspond to frequencies of 30 to 60 Hz, 15 to 30 Hz and 0 to 15 Hz, respectively.

The 20-second raw signal prior to the alarm was decomposed via the multi-level wavelet transform into the three sub signals, WA4 510, WD4 512 and WD3 514. The wide QRS complex of the ventricular beats was captured mostly by the lower frequency signal, WA4 510, and somewhat captured by WD4 512. The signals, WD4 512 and WD3 514, encode the noise of the signal.

The features that were extracted from the wavelet transform fall under five categories:

(a) Summary statistics of each signal. The mean, standard deviation, skewness and kurtosis were extracted.

(b) Absolute area under the curve or sum of entries of the signal. For lower frequencies, this measurement captured the wideness of QRS complexes, whereas in high frequencies, it accounted for the noise.

(c) Number of times signal takes on values close to zero. Many crossings of the signal in this value encoded noise.

(d) Capturing of the ventricular beats. The signal WA4 was subdivided into intervals of approximately 20 seconds in length and the absolute area under the curve of each of these subintervals was computed. The mean, the standard deviation, skewness and kurtosis were obtained from the 10 highest numbers, which were meant to represent the ventricular beats candidates.

Figure 7A:
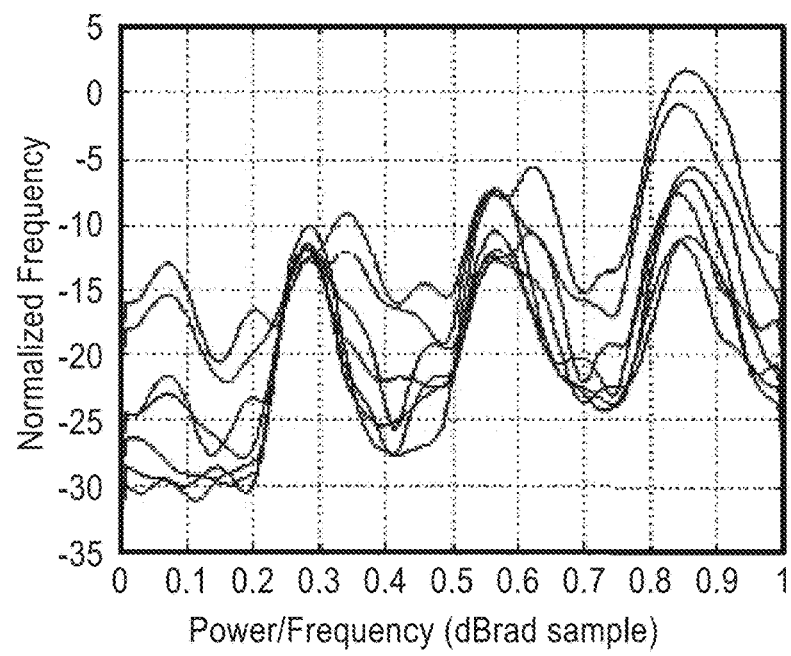
FIG. 7A is a plot showing the power spectral densities (PSD) of all 7 leads in a false VT alarm.
Figure 7B:
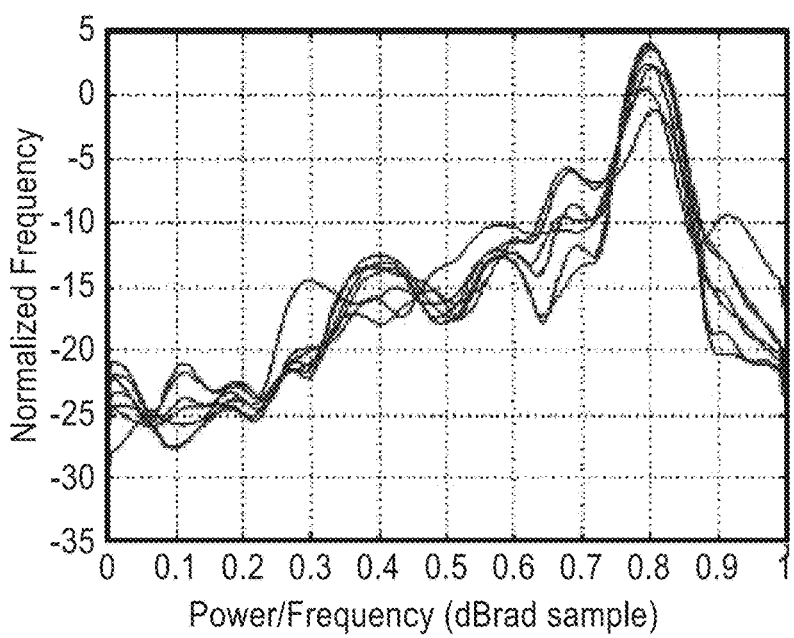
FIG. 7B is a plot showing the PSD of all 7 leads in a true VT alarm.

(e) Summary statistics of pairwise distance between leads. To measure the difference between every pair of leads, the frequency distributions or power spectral densities (PSD) were compared. FIG. 7A shows the PSD of all 7 ECG leads in a false VT alarm. FIG. 7B shows the PSD of all 7 ECG leads in a true VT alarm. We computed the PSD estimate of the input signal using Welch's averaged, modified periodogram method. The signal was divided into 200 windows with 50% overlap, each section is windowed with a Hamming window and eight modified periodograms are computed and averaged, as described in the MATLAB documentation. Afterwards, the symmetric KL-divergence between every pair of signals was computed, given by:

$$KLdiv_{sym} = \frac{1}{2}\left[\sum_i p(t_i)\log\left(\frac{p(t_i)}{q(t_i)}\right) + \sum_i q(t_i)\log\left(\frac{q(t_i)}{p(t_i)}\right)\right]$$

When all seven leads are available, computing their pairwise distances results in 21 numbers total. We extracted the mean, standard deviation, skewness and kurtosis of these 21 numbers.

Features in all five categories were extracted from only the low frequency signal, WA4. Features in categories (a), (b) and (e) were extracted from the WD3 signal. Signal WD4 was only represented with features from category (b). It is important to point out that the features from categories (a) through (d) were produced for each available lead in the 20 second segment prior to the alarm. However, the number of available leads can vary between different alarms.

Figure 8:
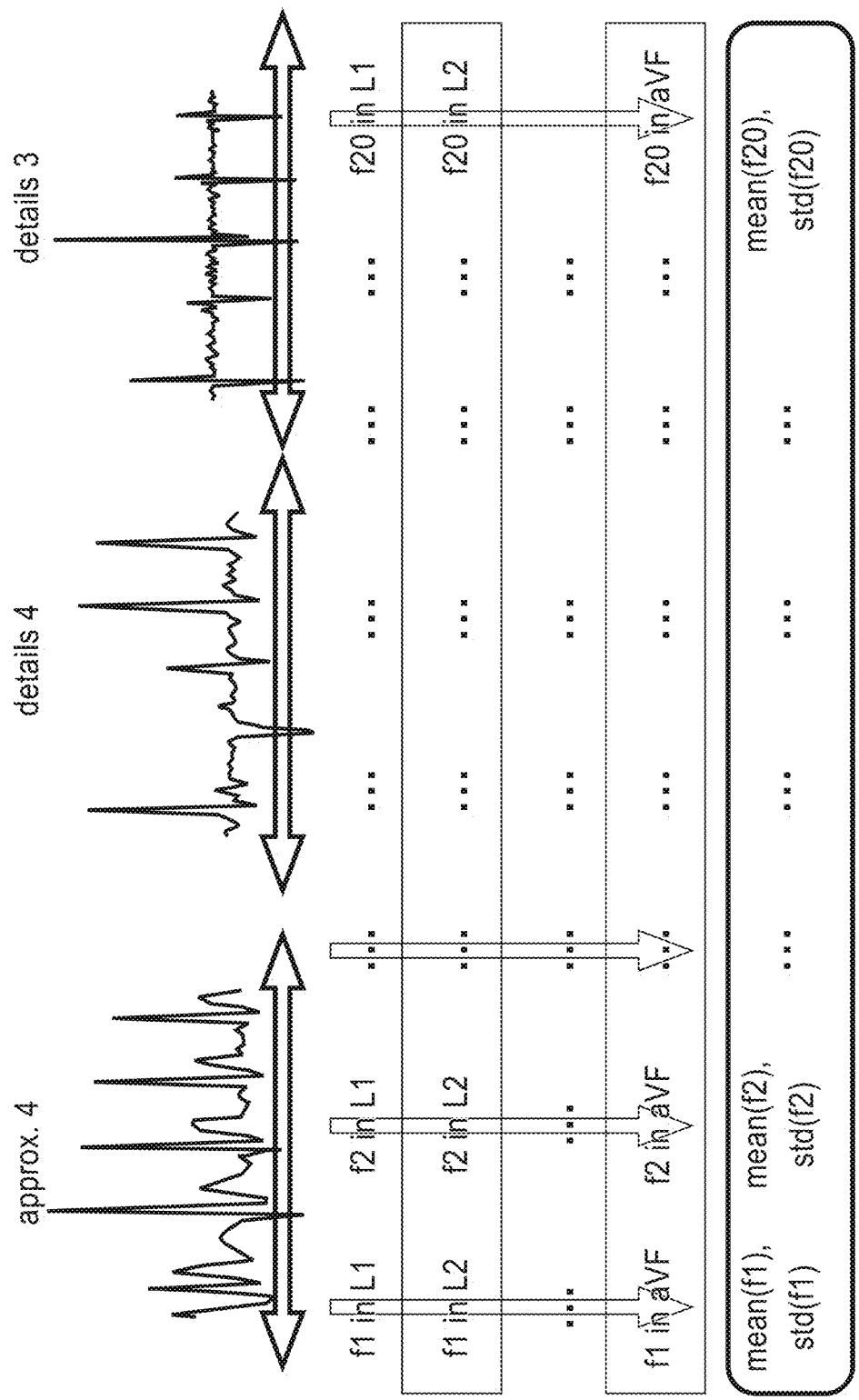
FIG. 8 is a schematic diagram of features being combined across all of the signals from all ECG leads.

Twenty features in categories (a) through (d) were extracted per ECG lead. However, because not all of the seven possible ECG leads were present for every patient or available during the 20 second window considered for this example, the features (f1, f2, . . . f20) extracted from the waveform data from each lead were combined by reporting both the mean and standard deviation among all leads (L1, L2), as shown in FIG. 8. The mean of all lead data gives a combined value for all available leads, whereas the standard deviation helps to determine whether there is a high variability within these features among lead waveform data. The total number of features per alarm was 48. Of these features, 20 were for the mean values and 20 were for the standard deviation among leads of features from categories (a) through (d). Eight features corresponded to features in the (e) category.

It should be appreciated that the presently described method can be used with different types of patient monitors, however, achieving optimal performance for different types of patient monitor alarms would require different features to be extracted from ECG and other related physiological signals.

The classification task was performed using L1 regularized Logistic Regression, one of the most robust and quickly trained classifiers, highlighting the fact that the novel features extracted in this embodiment of the presently described method do carry enough descriptive power to differentiate between true and false VT alarms. It should be appreciated, however, that other classifiers may be used.

A classifier was trained using 80% of the data and its performance was tested using the remaining 20%. Preliminary results showed that 46% of the false alarms could be eliminated while 97% of the true alarms could be retained.

Separate classifier analyses were conducted for the UCSF-GE dataset and for the MIMIC II dataset. The classifier investigated was L1-regularized Logistic Regression (LR). This classifier was chosen because it encourages sparse coefficients for the features and scales well with the number of features and the size of the dataset. It is also fairly robust, provides a linear decision boundary, and has only one hyperparameter. Although a simpler classifier may offer good performance, using a simpler classifier would also stress the predictive power of the extracted features.

Figure 9:
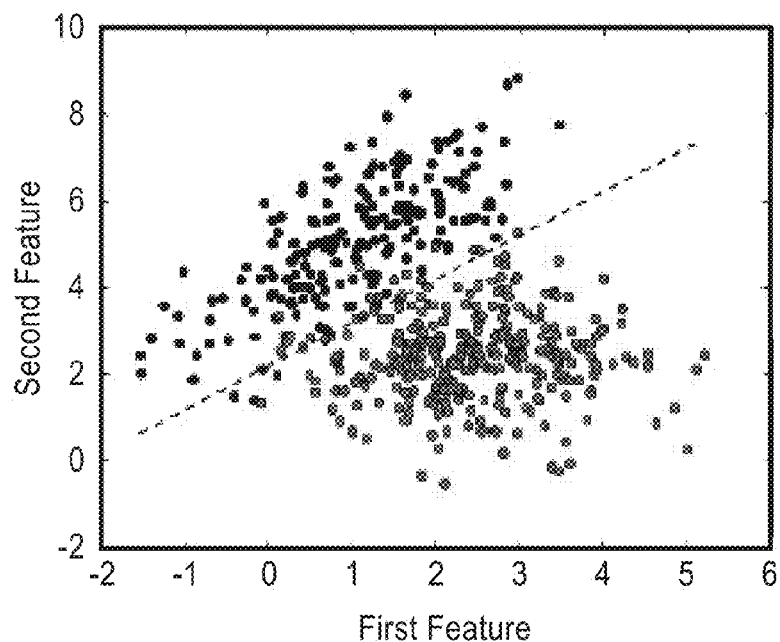
FIG. 9 is a plot of a training set used to determine the hyperparameter C (the inverse of regularization strength) by performing 5-fold cross validation.

A training set, as shown in FIG. 9, was used to determine the hyperparameter C (the inverse of regularization strength) by performing 5-fold cross validation. A grid search was performed in the hyperparameter space, where the values for C were exponentially spaced. A more refined search was performed near the best values for C. Another issue tackled was that of having an unbalanced dataset where only a small percentage of the alarms are true. Therefore, class weights were used that were inversely proportional to the class frequencies in the training set, which oversam pled the underrepresented class in the training set.

In order to train the classifiers, each 20 second ECG segment was represented by a vector. The set Xtrain was normalized so that it would have mean zero and variance one across each feature. Afterwards, Xtest was normalized using the mean and variance of Xtrain.

For the UCSF dataset, the training set, Xtrain, consisted of 979 alarms and the test set, Xtest, consisted of 294 alarms. For the MIMIC II dataset, the training set, Xtrain, consisted of 822 alarms, and the test set, Xtest, consisted of 200 alarms. The analysis was carried out using Python Scikit-Learn.

Figure 10:
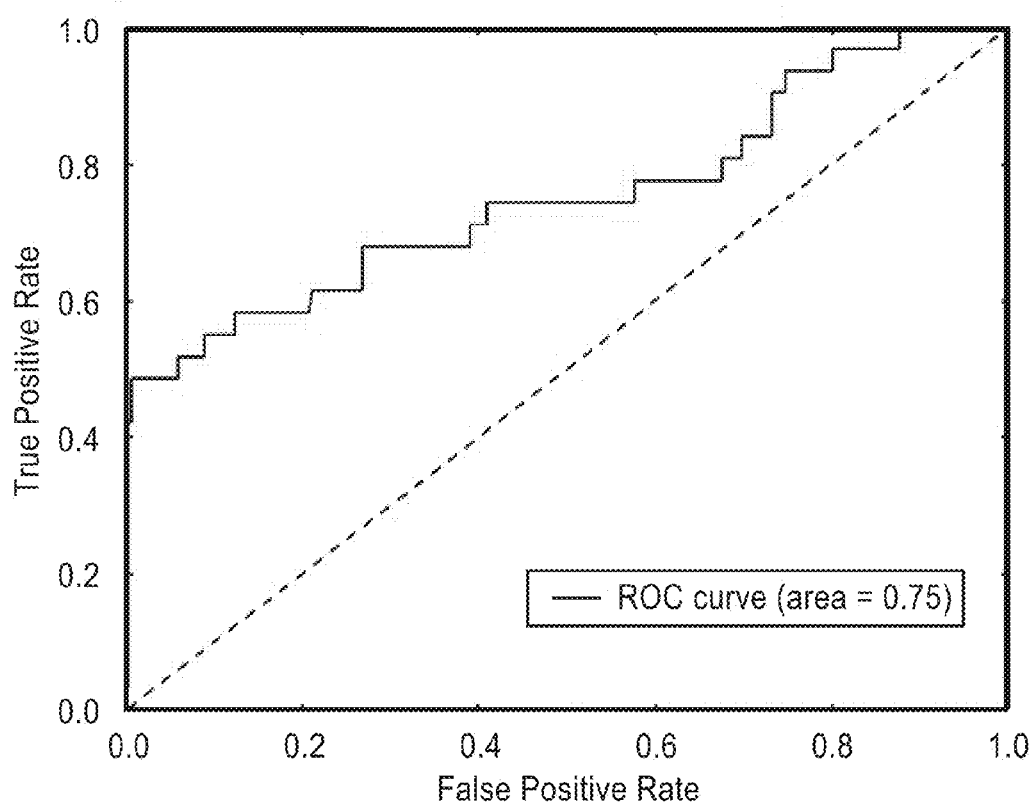
FIG. 10 is a plot of the Receiver Operating Characteristic (ROC) curve for the UCSF-GE database with a patient monitor false alarm (FA) suppression of 36% with zero true VT alarm (TA) suppression.
Figure 11:
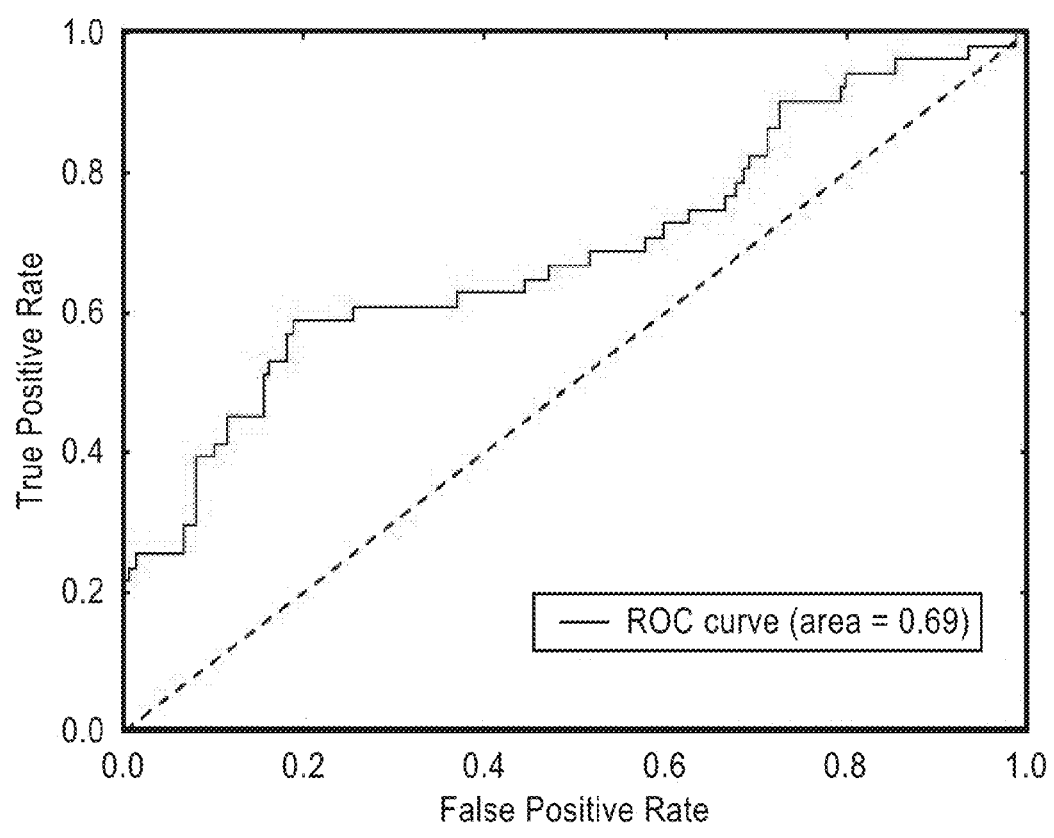
FIG. 11 is a plot of the ROC curve for the MIMIC II dataset with a FA suppression of 21% and zero TA suppression.

FIG. 10 and FIG. 11 show the Receiver Operating Characteristic (ROC) curves, which depict the performance of the classifiers on the test set for both the UCSF and MIMIC II datasets, respectively. The test set in both the UCSF data and the MIMIC II data consists of different patients than those in the training set. For both datasets, the best performing classifier was L1-regularized LR.

FIG. 10 shows the ROC curve for the UCSF-GE database with a FA suppression of 36% with zero true VT alarm (TA) suppression. If 5% of TA is suppressed, there is a 40% FA suppression. When applying the algorithm to the UCSF-GE dataset, a higher FA suppression (35.5%, with 0% TA suppression and 48.4% with TA suppression of less than 1%) was achieved than for the MIMIC II dataset. The fact that the UCSF-GE data contained seven ECG signals in the 20 sec prior to the alarm, instead of three signals in the MIMIC II dataset, may have contributed to the accuracy of the FA detection.

A FA suppression of 21% was obtained for the MIMIC II database with zero TA suppression. It should be noted that different groups reported results in different subsets of this dataset, making a direct comparison less straightforward. Moreover, certain approaches required an invasive arterial monitoring waveform, which selects for a sedated and less mobile patient population, thus decreasing the motion artifacts in the signals. The corresponding ROC curve is shown in FIG. 11. Allowing for a 1% TA suppression rate, a 24.7% FA suppression is obtained. A 38% FA suppression would incur in an 8% TA suppression.

Advantages of the presently described method embodiments are that they use only ECG signals and do not require R-peak detection. Using only ECG makes the algorithm feasible for monitoring applications outside the ICU where additional invasive waveforms are not available. In the UCSF-GE dataset, one of the main causes for triggering VT alarms was likely artifact mimicking true VT in one or more ECG leads. This seems to be exaggerated if these leads also have low QRS amplitude. Another explanation for FA is bundle branch block (BBB) with a heart rate (HR) of over 100 beats per minute. The present method performed poorly in rejecting false VT alarms of patients with BBB. Future work should address the problem of differentiating between true VT and BBB with a fast HR.

An example embodiment of a method to reduce the number of case VT alarms in the ICU has been described that is based on novel features extracted from a multi resolution wavelet transform 20 seconds prior to the alarm trigger. However, the method described herein can be implemented to reduce the number of false monitor alarms in other arrhythmias.

Figure 12:
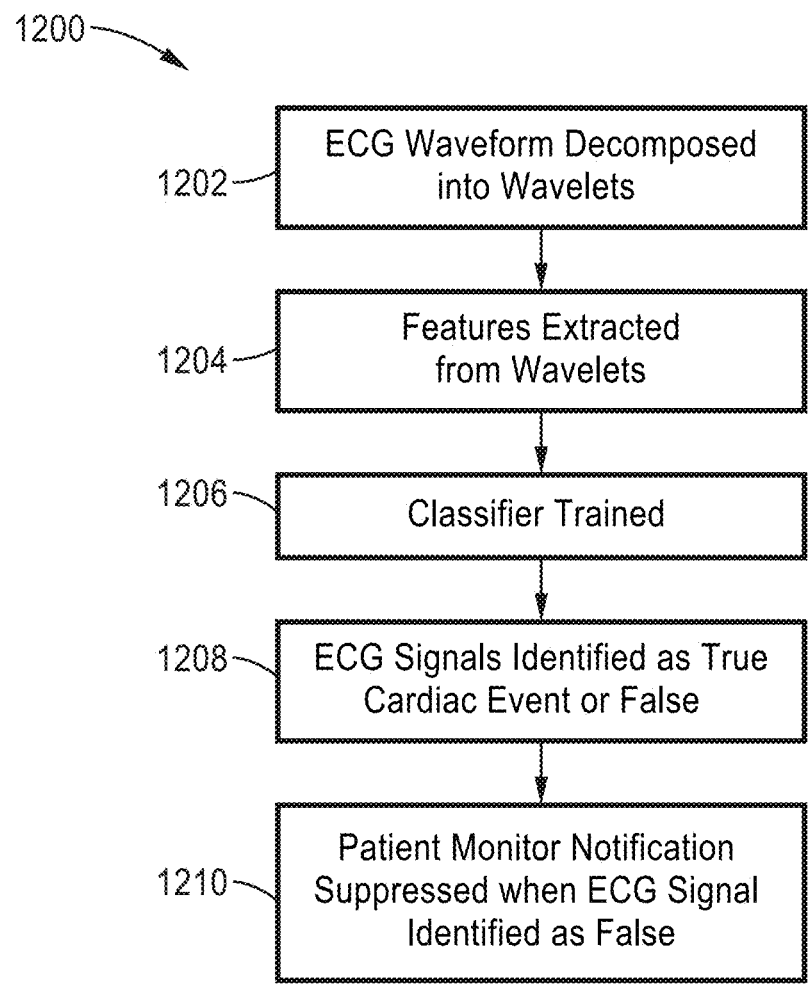
FIG. 12 is a flow diagram of an embodiment of the presently described method.

In FIG. 12, an embodiment of the presently described method is illustrated in a flow diagram 1200. First, a waveform from an ECG is decomposed into wavelets to separate the signal into approximation wavelets and detail wavelets 1202. Next, features are extracted from the lower dimensional signals 1204. These features may include statistics and how they vary among ECG leads, the absolute area under the curve, the number of times a signal reaches values close to zero, capturing of ventricular beats, summary statistics of pairwise distance between leads and any other features useful for distinguishing a true and false VT. A classifier can also be trained 1206 and its performance can be evaluated. ECG signals can be identified as true cardiac events, such as VT, or false, non-events 1208. The patient monitor notification can then be suppressed when an ECG (or other monitor signal) is identified as false 1210.

The enhancements described in the presented technology can be readily implemented within various patient monitors and more particularly, cardiac monitors. It should also be appreciated that patient monitors are preferably implemented to include one or more computer processor devices (e.g., CPU, microprocessor, microcontroller, computer enabled ASIC, etc.) and associated memory storing instructions (e.g., RAM, DRAM, NVRAM, FLASH, computer readable media, etc.) whereby programming (instructions) stored in the memory are executed on the processor to perform the steps of the various process methods described herein.

The computer and memory devices were not depicted in the diagrams for the sake of simplicity of illustration, as one of ordinary skill in the art recognizes the use of computer devices for carrying out steps involved with image/video encoding and decoding. The presented technology is non-limiting with regard to memory and computer-readable media, insofar as these are non-transitory, and thus not constituting a transitory electronic signal.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A method for determining whether a pathophysiological signal is true or false, the method comprising: receiving physiological waveform data from a patient monitor, said patient monitor configured to collect multiple waveform data and provide notification to an operator when it detects a pathophysiological signal; extracting at least one multiresolution wavelet transform from the physiological waveform data of said multiple waveform data; extracting at least one feature from said multiresolution wavelet transform; analyzing variations among said at least one extracted feature for said multiple waveform data to determine whether the pathophysiological signal is true or false; training a classifier by presenting said at least one extracted feature to said classifier; and suppressing said notification when it is determined that the pathophysiological signal is false.

2. The method of any preceding embodiment, wherein the waveform data comprises a signal that is approximately 20 seconds in length prior to said patient monitor notifying the operator of a pathophysiological signal.

3. The method of any preceding embodiment, wherein the multiresolution transforms include the levels of details wavelet 3 (WD3), details wavelet 4 (WD4) and approximation wavelet 4 (WA4).

4. The method of any preceding embodiment, wherein said at least one feature is selected from a group of features consisting of mean, standard deviation, skewness, kurtosis, absolute area under the curve, number of times a signal takes on values close to zero, ventricular beats, and summary statistics of pairwise distance between leads.

5. A method for determining whether an electrocardiogram (ECG) arrhythmia signal is true or false, the method comprising: receiving ECG waveform data from a patient monitor, said patient monitor configured to collect waveform data from multiple ECG leads and provide notification to an operator when it detects an ECG signal of arrhythmia; extracting at least one multiresolution wavelet transform from the ECG waveform data of said multiple ECG leads; extracting at least one feature from said multiresolution wavelet transform; analyzing variations among said at least one extracted feature for said multiple ECG leads to determine whether the ECG waveform data is a true or a false arrhythmia; training a classifier by presenting said at least one extracted feature to said classifier; and suppressing said notification when it is determined that the ECG waveform data is a false arrhythmia.

6. The method of any preceding embodiment, wherein the arrhythmia comprises ventricular tachycardia (VT).

7. The method of any preceding embodiment, wherein extracting the at least one multiresolution wavelet transform is performed using a Discrete Wavelet Transform.

8. The method of any preceding embodiment, wherein the ECG waveform data comprises a signal that is approximately 20 seconds in length prior to said patient monitor notifying the operator of an ECG signal of arrhythmia.

9. The method of any preceding embodiment, wherein the multiresolution transforms include the levels of details wavelet 3 (WD3), details wavelet 4 (WD4) and approximation wavelet 4 (WA4).

10. The method of any preceding embodiment, wherein extracting at least one feature from said wavelet details 3 (WD3), wavelet details 4 (WD4) and wavelet approximation 4 (WA4) comprises: extracting the mean, standard deviation, skewness, kurtosis, absolute area under the curve, number of times a signal takes on values close to zero, ventricular beats, and summary statistics of pairwise distance between leads from WA4; extracting the mean, standard deviation, skewness, kurtosis, absolute area under the curve, and summary statistics of pairwise distance between leads from WD3; and extracting the absolute area under the curve from WD4.

11. The method of any preceding embodiment, wherein said at least one feature is selected from a group of features consisting of mean, standard deviation, skewness, kurtosis, absolute area under the curve, number of times a signal takes on values close to zero, ventricular beats, and summary statistics of pairwise distance between leads.

12. The method of any preceding embodiment, wherein the classifier comprises a L1 regularized Logistic Regression.

13. A computer implemented method for determining whether an ECG arrhythmia signal is true or false, the method comprising: receiving electrocardiogram (ECG) waveform data from a patient monitor, said patient monitor configured to collect waveform data from multiple ECG leads and provide notification to an operator when it detects an ECG signal of arrhythmia; extracting at least one multiresolution wavelet transform from the ECG waveform data of said multiple ECG leads; extracting at least one feature from said multiresolution wavelet transform; analyzing variations among extracted features for said multiple ECG leads to determine whether the ECG waveform data is a true or a false arrhythmia; training a classifier by presenting said at least one extracted feature to said classifier; and suppressing notification when it is determined that the ECG waveform data is a false arrhythmia; wherein said method is performed by executing instructions, on at least one computer processor, said instructions residing in a non-transitory memory readable by the computer processor.

14. The method of any preceding embodiment, wherein the arrhythmia comprises ventricular tachycardia (VT).

15. The method of any preceding embodiment, wherein said programming is further configured to extract the at least one multiresolution wavelet transform is performed using a Discrete Wavelet Transform.

16. The method of any preceding embodiment, wherein the ECG waveform data comprises a signal that is approximately 20 seconds in length prior to said patient monitor notifying the operator of an ECG signal of arrhythmia.

17. The method of any preceding embodiment, wherein the multiresolution transforms include the levels of: wavelet details 3 (WD3), wavelet details 4 (WD4) and wavelet approximation 4 (WA4).

18. The method of any preceding embodiment, wherein extracting at least one feature from said wavelet details 3

(WD3), wavelet details 4 (WD4) and wavelet approximation 4 (WA4) comprises: extracting the mean, standard deviation, skewness, kurtosis, absolute area under the curve, number of times signal takes on values close to zero, ventricular beats, and summary statistics of pairwise distance between leads from WA4; extracting the mean, standard deviation, skewness, kurtosis, absolute area under the curve, and summary statistics of pairwise distance between leads from WD3; and extracting the absolute area under the curve from WD4.

19. The method of any preceding embodiment, wherein said at least one feature is selected from a group of features consisting of mean, standard deviation, skewness, kurtosis, absolute area under the curve, number of times signal takes on values close to zero, ventricular beats, and summary statistics of pairwise distance between leads.

20. The method of any preceding embodiment, wherein the classifier comprises a L1 regularized Logistic Regression.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for." No claim element herein is to be construed as a "step plus function" element unless the element is expressly recited using the phrase "step for."

TABLE 1

Summary of Datasets

| Dataset | Number of Alarms/percentage of true alarms | Number of ECG leads per patient |
| --- | --- | --- |
| MIMIC II | 1,088 27% true | 3 |
| UCSF-GE | 1,253 alarms 10% true | 7 |

What is claimed is:

1. A method for determining whether a cardiac arrhythmia signal is true or false, the method comprising:
    receiving physiological waveform data from a patient monitor, said patient monitor configured to collect multiple waveform data and provide notification to an operator when it detects a cardiac arrhythmia signal;
    extracting at least one multiresolution wavelet transform from the physiological waveform data of said multiple waveform data;
    extracting at least one feature from said multiresolution wavelet transform, wherein extracting said at least one feature comprises isolating specified frequency bands within said multiresolution wavelet transform;
    analyzing variations among said at least one extracted feature for said multiple waveform data to determine whether the pathophysiological signal is true or false;
    training a classifier by presenting said at least one extracted feature to said classifier; and
    suppressing said notification when it is determined that the cardiac arrhythmia signal is false.

2. The method of claim 1, wherein the waveform data comprises a signal that is approximately 20 seconds in length prior to said patient monitor notifying the operator of a cardiac arrhythmia signal.

3. The method of claim 1, wherein the at least one feature is extracted from each of the multiresolution transforms levels: details wavelet 3 (WD3), details wavelet 4 (WD4) and approximation wavelet 4 (WA4).

4. The method of claim 1, wherein said physiological waveform data is acquired from multiple leads coupled to the monitor;
    wherein said at least one feature comprises variances in said frequency bands across the multiple leads.

5. A method for determining whether an electrocardiogram (ECG) arrhythmia signal is true or false, the method comprising:
    receiving ECG waveform data from a patient monitor, said patient monitor configured to collect waveform data from multiple ECG leads and provide notification to an operator when it detects an ECG signal of arrhythmia;
    extracting at least one multiresolution wavelet transform from the ECG waveform data from each of said multiple ECG leads;
    extracting at least one feature from said multiresolution wavelet transform;
    analyzing variations among said at least one extracted feature between each of said multiple ECG leads to determine whether the ECG waveform data is a true or a false arrhythmia;
    training a classifier by presenting said at least one extracted feature to said classifier; and
    suppressing said notification when it is determined that the ECG waveform data is a false arrhythmia.

6. The method of claim 5, wherein the arrhythmia comprises ventricular tachycardia (VT).

7. The method of claim 5, wherein extracting the at least one multiresolution wavelet transform is performed using a Discrete Wavelet Transform.

8. The method of claim 5, wherein the ECG waveform data comprises a signal that is approximately 20 seconds in length prior to said patient monitor notifying the operator of an ECG signal of arrhythmia.

9. The method of claim 5, wherein the at least one feature is extracted from each of the multiresolution transforms include levels: details wavelet 3 (WD3), details wavelet 4 (WD4) and approximation wavelet 4 (WA4).

10. The method of claim 9, wherein extracting at least one feature from said wavelet details 3 (WD3), wavelet details 4 (WD4) and wavelet approximation 4 (WA4) comprises:
    extracting the mean, standard deviation, skewness, kurtosis, absolute area under the curve, number of times a signal takes on values close to zero, ventricular beats, and summary statistics of pairwise distance between leads from WA4;

extracting the mean, standard deviation, skewness, kurtosis, absolute area under the curve, and summary statistics of pairwise distance between leads from WD3; and extracting the absolute area under the curve from WD4.

11. The method of claim 5, wherein said at least one feature is selected from a group of features consisting of mean, standard deviation, skewness, kurtosis, absolute area under the curve, number of times a signal takes on values close to zero, ventricular beats, and summary statistics of pairwise distance between leads.

12. The method of claim 5, wherein the classifier comprises a L1 regularized Logistic Regression.

13. A computer implemented method for determining whether an ECG arrhythmia signal is true or false, the method comprising:
  receiving electrocardiogram (ECG) waveform data from a patient monitor, said patient monitor configured to collect waveform data from multiple ECG leads and provide notification to an operator when it detects an ECG signal of arrhythmia;
  extracting at least one multiresolution wavelet transform from the ECG waveform data from each of said multiple ECG leads;
  extracting at least one feature from said multiresolution wavelet transform;
  analyzing variations among extracted features between each of said multiple ECG leads to determine whether the ECG waveform data is a true or a false arrhythmia;
  training a classifier by presenting said at least one extracted feature to said classifier; and
  suppressing notification when it is determined that the ECG waveform data is a false arrhythmia;
  wherein said method is performed by executing instructions, on at least one computer processor, said instructions residing in a non-transitory memory readable by the computer processor.

14. The method of claim 13, wherein the arrhythmia comprises ventricular tachycardia (VT).

15. The method of claim 13, wherein said programming is further configured to extract the at least one multiresolution wavelet transform is performed using a Discrete Wavelet Transform.

16. The method of claim 13, wherein the ECG waveform data comprises a signal that is approximately 20 seconds in length prior to said patient monitor notifying the operator of an ECG signal of arrhythmia.

17. The method of claim 13, wherein the at least one feature is extracted from each of the multiresolution transforms levels: wavelet details 3 (WD3), wavelet details 4 (WD4) and wavelet approximation 4 (WA4).

18. The method of claim 17, wherein extracting at least one feature from said wavelet details 3 (WD3), wavelet details 4 (WD4) and wavelet approximation 4 (WA4) comprises:
  extracting the mean, standard deviation, skewness, kurtosis, absolute area under the curve, number of times signal takes on values close to zero, ventricular beats, and summary statistics of pairwise distance between leads from WA4;
  extracting the mean, standard deviation, skewness, kurtosis, absolute area under the curve, and summary statistics of pairwise distance between leads from WD3; and
  extracting the absolute area under the curve from WD4.

19. The method of claim 13, wherein said at least one feature is selected from a group of features consisting of mean, standard deviation, skewness, kurtosis, absolute area under the curve, number of times signal takes on values close to zero, ventricular beats, and summary statistics of pairwise distance between leads.

20. The method of claim 13, wherein the classifier comprises a L1 regularized Logistic Regression.

* * * * *